United States Patent [19]
Kriesel et al.

[11] Patent Number: 5,514,090
[45] Date of Patent: May 7, 1996

[54] CLOSED DRUG DELIVERY SYSTEM

[75] Inventors: Marshall S. Kriesel, Saint Paul; Thomas N. Thompson, Richfield, both of Minn.

[73] Assignee: Science Incorporated, Bloomington, Minn.

[21] Appl. No.: 284,357

[22] Filed: Aug. 2, 1994

Related U.S. Application Data

[63] Continuation-in-part of Ser. No. 54,152, Apr. 26, 1993, Pat. No. 5,336,180, which is a continuation-in-part of Ser. No. 34,908, Mar. 19, 1993, Pat. No. 5,328,464, which is a continuation-in-part of Ser. No. 870,553, Apr. 17, 1992, Pat. No. 5,267,957, which is a continuation-in-part of Ser. No. 513,917, Apr. 24, 1990, Pat. No. 5,122,116.

[51] Int. Cl.$^6$ .................................................. A61M 37/00
[52] U.S. Cl. ........................... 604/85; 604/86; 604/132; 604/153; 604/246; 604/890.1; 128/DIG. 12
[58] Field of Search .................................. 604/82, 83, 85, 604/86, 89, 122, 123, 131, 132, 151, 153, 246, 415, 416, 890.1; 128/DIG. 12

[56] References Cited

U.S. PATENT DOCUMENTS

| | | | |
|---|---|---|---|
| 4,968,301 | 11/1990 | diPalma et al. | 604/132 |
| 5,176,641 | 1/1993 | Idriss | 604/133 |
| 5,205,820 | 4/1993 | Kriesel | 604/85 |
| 5,236,418 | 8/1993 | Kriesel | 604/85 |
| 5,257,987 | 11/1993 | Athayde et al. | 604/892.1 |
| 5,263,935 | 11/1993 | Hessel | 604/132 |
| 5,336,188 | 8/1994 | Kriesel | 604/132 |

*Primary Examiner*—Corrine M. McDermott
*Attorney, Agent, or Firm*—James E. Brunton

[57] ABSTRACT

An apparatus for controllably intermixing two or more components in a sterile, closed environment to produce a flowable substance and then for expelling the flowable substance from the apparatus at a precisely controlled rate. The apparatus is particularly useful for medical applications and includes a dispenser portion with its own stored energy member for dispensing the flowable mixture and a coupling mechanism for coupling a drug vial to the dispenser portion for the controlled mixing of a medicament contained within the drug vial with a diluent stored within the dispenser portion of the apparatus via a sterile pathway.

29 Claims, 5 Drawing Sheets

CLOSED DRUG DELIVERY SYSTEM

This is a Continuation In Part Application of Ser. No. 08/054,152, filed Apr. 26, 1993 now U.S. Pat. No. 5,336,180; which is a Continuation In Part of Ser. No. 08/034,908, filed Mar. 19, 1993, now U.S. Pat. No. 5,328,464; which is a Continuation In Part of Ser. No. 07/870,553, filed Apr. 17, 1992, now U.S. Pat. No. 5,267,957; which is a Continuation In Part of Ser. No. 07/513,917, filed Apr. 24, 1990, now U.S. Pat. No. 5,122,116.

BACKGROUND OF THE INVENTION

1. Field of the Invention

The present invention relates generally to fluid mixing and delivery systems. More particularly, the invention concerns an apparatus for intermixing selected medicaments to form a flowable substance and for then infusing the substance into a patient at a precisely controlled rate.

2. Discussion of the Invention

Medicament delivering systems that can separately store and then controllably intermix a selected medicament with a diluent for infusion into a patient at a controlled rate have come into wide use. In the prior art systems the diluent is generally packaged in flexible plastic containers having administration ports for connection to an administration set which delivers the container contents from the container to the patient. The drug is often packaged in a separate, closed container and is mixed with the diluent shortly before infusion of the medicament in the patient.

Drugs are typically packaged separately from the diluent for a number of reasons. One important reason is that certain drugs do not retain their efficacy when mixed with a diluent and, therefore, the mixture cannot be stored for any appreciable length of time. Another reason is that many drug manufacturers do not produce medical fluids in containers for intravenous delivery. As a general rule, drugs are packaged in powder form in small, closed containers, or vials, for later mixing with a suitable diluent. In many instances it is necessary to mix the drug with the diluent immediately prior to delivery to the patient to insure that the drug will not separate from the diluent prior to or during infusion.

Infusion of medicaments is most often accomplished in a hospital environment and the nurse, doctor or other medical personnel mixes the drug and diluent shortly before administration of the drug to the patient. This mixing step can be time consuming and hazardous, as for example, when toxic drugs are used. Additionally, many of the prior art mixing devices are crude and imprecise making accurate, sterile and thorough mixing of the drug and the diluent difficult, time consuming and not well suited for use in the home environment.

Several types of closed drug delivery systems are presently in use. These systems typically comprise a flexible container such as a plastic bag to which a drug vial can be coupled. The flexible container usually contains a liquid diluent and often includes a frangible member that allows fluid passage only when broken. When the drug vial is coupled with the flexible container, the stopper of the drug vial is pierced and the frangible member ruptured so as to allow sterile communication between the drug vial and the liquid diluent contents of the flexible container. Mixing of the drug with the diluent is accomplished by manipulating the flexible container. Exemplary of prior art systems of the aforementioned character are those disclosed in U.S. Pat. No. 4,583,971 issued to Bocquet, et al. and in U.S. Pat. No. 4,606,734 issued to Larkin.

Another prior art closed delivery and mixing system is disclosed in U.S. Pat. No. 4,458,733 issued to Lyons. The Lyons apparatus includes a compressible chamber with a liquid component therein, the compressible chamber including gas-trapping and reservoir compartments in open communication. The gas trapping compartment can be connected to a container such as a drug vial having a mixing component therein. After a pathway between the vial and the gas trapping compartment is opened, mixing is accomplished through manipulation of the compressible chamber.

Another very successful prior art, dual container system is described in U.S. Pat. Nos. 4,614,267 issued to Larkin and 4,614,515 issued to Tripp and Larkin. In this system, a flexible diluent container includes a tubular port which provides means for securing thereto a stoppered medicament vial as well as a stopper removal means. The stopper removal means includes an engagement element, or extractor, which is attached to a removable cover and seals the inner end of the port. In use, as the vial is advanced into the tubular port, the vial stopper moves into engagement with the extractor which grips the stopper enabling it to be pulled from the vial as the cover is pulled from the port. Once the stopper has been removed from the vial, the contents of the vial can be dumped into the diluent in the bag and mixed therewith through manipulation of the bag.

The prior art devices of the character described in the preceding paragraphs typically use the traditional gravity flow method for infusion of the medicament mixture into the patient. Such a method is cumbersome, imprecise and typically requires bed confinement of the patient. Also, the flexible bag must be maintained in a substantially elevated position and periodic monitoring of the apparatus by the nurse or doctor is required to detect malfunctions of the infusion apparatus.

The apparatus of the present invention overcomes the drawbacks of the prior art by totally eliminating the need for a flexible bag, the cumbersome manipulative mixing of the medicaments using the flexible bag and the undesirable gravity infusion method which is typically followed when the flexible bag is used.

As discussed in detail in co-pending U.S. Ser. No. 08/054,152 which was filed by the present inventors and in U.S. Pat. No. 5,328,464, issued to the present inventors, the material used in the apparatus of the present invention include recently developed elastomeric films and laminates of these films, which, in cooperation with a base define a fluid chamber that contains the fluid to which various additives are added prior to the mixture being dispensed.

The elastomeric materials used, as well as various alternate forms of the apparatus of the invention, are described in detail in U.S. Ser. No. 08/054,152 filed Apr. 26, 1993 and in U.S. Pat. No. 5,328,464 issued to the present inventors. This application, as well as U.S. Pat. No. 5,328,464 are, therefore, hereby incorporated by reference in their entirety as though fully set forth herein.

DESCRIPTION OF THE INVENTION

Figures 1, 2, 2A, 4:
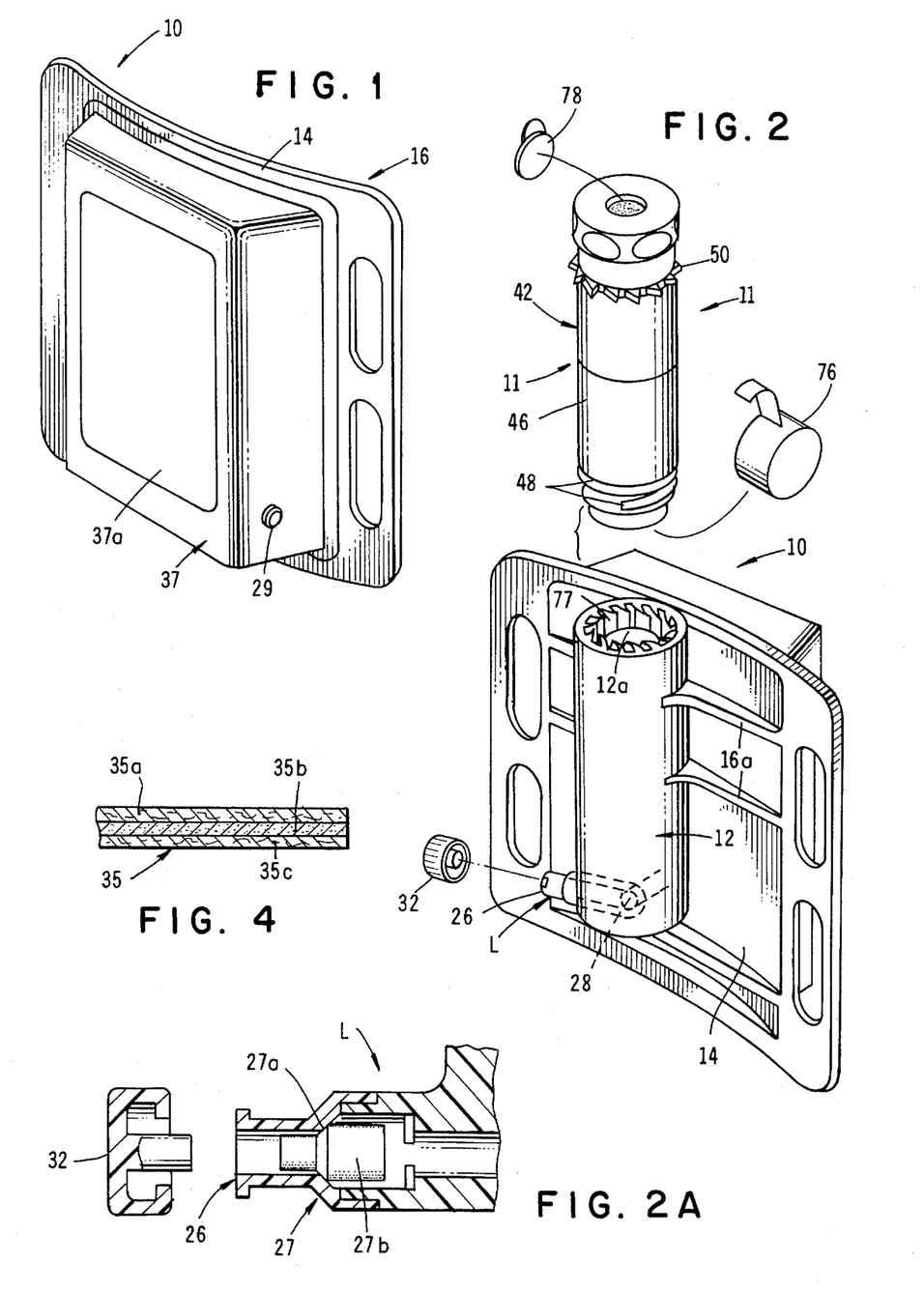
FIG. 1 is a generally perspective front view of one form of the dispensing portion of the device of the present invention.
FIG. 2 is a generally perspective, rear view of the dispensing portion of the device and showing by way of exploded view means the vial assembly of the invention.
FIG. 2A is an enlarged, cross-sectional view of the inlet port of the dispenser portion of the device.
FIG. 4 is a greatly enlarged cross-sectional view taken along lines 4—4 of FIG. 3.

Referring to FIGS. 1 through 5, one embodiment of the mixing apparatus of the present invention is there shown. This embodiment is similar in some respects to the embodiment shown in FIG. 67 through 70 of U.S. Pat. No. 5,324,464 and, as shown in FIGS. 1 and 2, includes a dispensing device 10 and a container assembly 11 which can be operably coupled with the dispensing device. However, this latest form of the invention is unique in that the fluid reservoir of the device is filled directly through a fluid inlet port provided in the dispenser portion of the apparatus rather than being filled via the vial subassembly. As before, when the fluid is introduced into the reservoir, an elastomeric membrane is distended so that it becomes the stored energy source for expelling the fluid from the reservoir. Fluid flowing from the reservoir flows toward into the medicament vial assembly portion of the device which is disposed within the cylindrical housing, or coupling means of the dispenser. As the fluid flows into the vial of the vial assembly, the additive contained within the vial is controllably mixed with the fluid flowing from the previously charged reservoir and the mixture thus formed is dispensed directly from the vial assembly via a delivery spike or similar accessing means.

As was the case with the embodiments described in Ser. No. 08/054,152, the present embodiment permits controlled intermixing of the first liquid component contained within the charged reservoir with the second component or additive contained within an additive presentation means of the character described in Ser. No. 08/054,152. However, rather than the infusible mixture being dispensed from the reservoir of the device, as was the case with the earlier described embodiments, here the mixture is dispensed directly from the vial assembly via appropriate vial accessing means.

Figure 5:
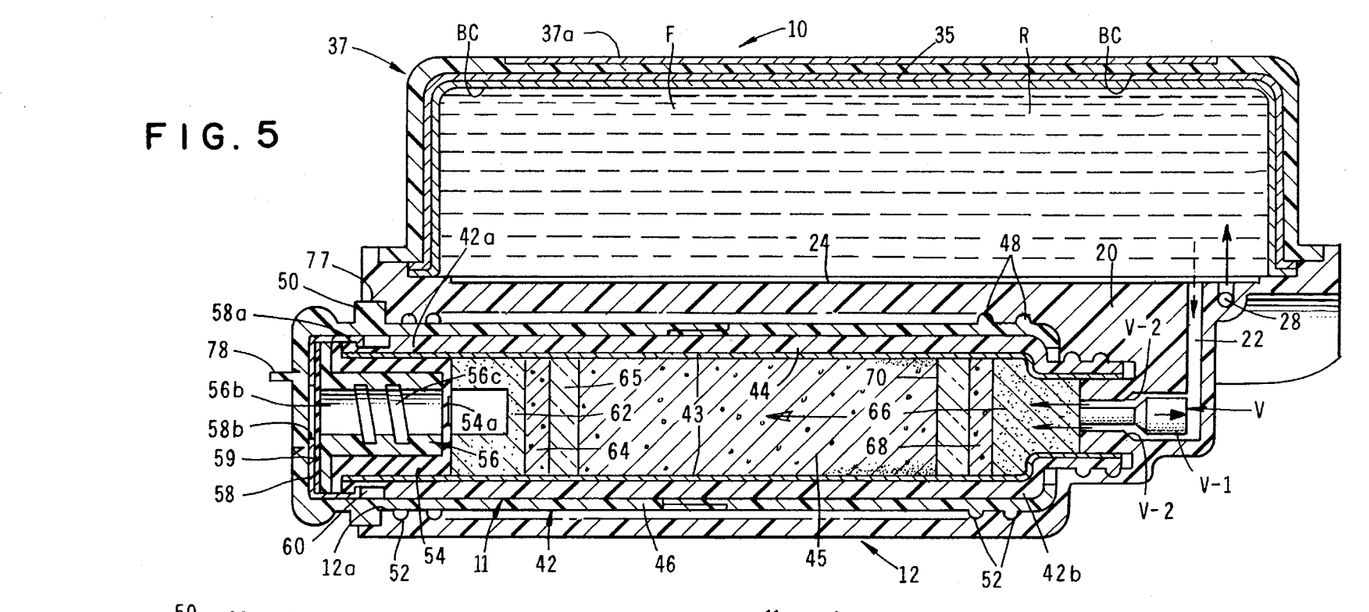
FIG. 5 is a greatly enlarged, side-elevational, cross-sectional view of the device of the invention shown with the vial assembly portion operably interconnected with the dispensing portion.

As best seen in FIGS. 1 and 2, in this latest form of the invention, the coupling means for coupling the vial assembly with the dispenser is similar to that described in U.S. Pat. No. 5,324,464 and comprises a cylindrical portion 12 which is connected to the back or concave surface 14 of a base member 16 by means of connector flanges 16a. Referring also to FIG. 5, it can be seen that portion 12 also includes a transversely extending base wall 20 having a flow passageway 22 which communicates with the storage reservoir R via a longitudinally extending passageway 24 provided in base member 16 (FIG. 3).

The inlet or reservoir filing port 26 of the device, which is in communication with reservoir R via passageway 28 (FIGS. 3 and 5), is preferably provided in the form of a luer check valve connector L of conventional design which is of the character shown in FIG. 2A. This type of connector includes a valve housing 27 having a valve seat 27a and a valve member 27b which is moved by fluid entering the inlet port from the closed position shown in FIG. 2A to an open position permitting fluid flow toward the reservoir R of the device. It is to be understood that, the inlet port can also comprise a non-coring, pierceable septum or various other types of filling devices well known in the art. However, when the luer connector is used, a cap 32 is provided to maintain the fluid path in a sterile condition.

Figure 3:
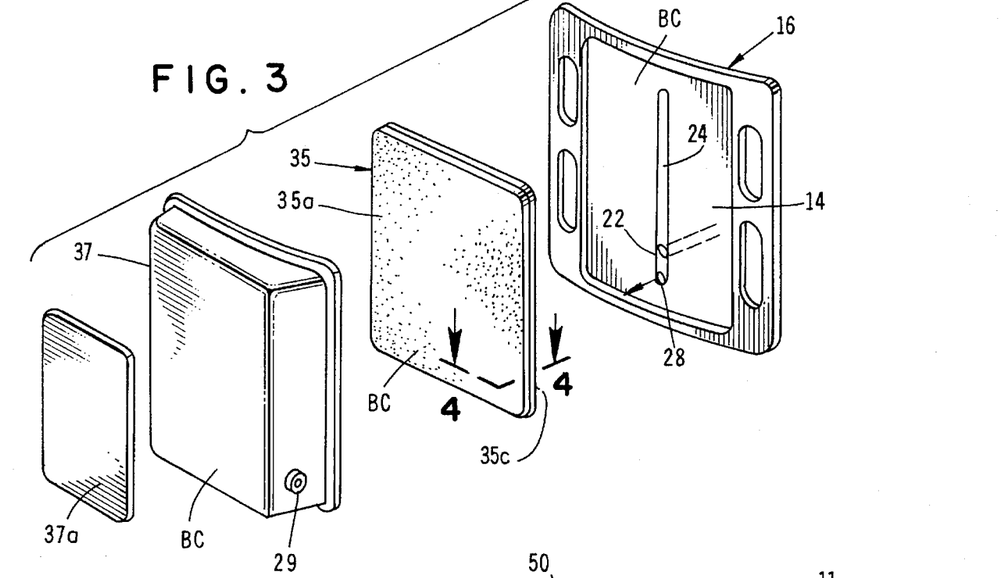
FIG. 3 is a generally perspective, exploded view of the dispensing portion of the device as shown in FIG. 1.

As indicated in FIGS. 3 and 4, the stored energy means of this latest form of the invention comprises a laminate construction 35 made up of a plurality of layers of elastomeric films 35a, 35b, and 35c. Reference should be made to Ser. No. 08/054,152 for a description of the various materials that can be used to construct the elastomeric films. Additionally, a somewhat similar laminate structure is disclosed in U.S. Pat. No. 5,169,389 issued to one of the present inventors wherein numerous materials are identified and discussed that are also suitable for the construction of laminate 35. Further materials suitable for constructing laminate 35 include a material sold by B-P Chemicals International of Cleveland, Ohio under the name and style "Barex", tetrafluoroethylenehexafluoropropylene and vinylidene fluoride (THV fluoroplastic) and other advanced barrier structure materials.

By constructing the stored energy means from a composite of several distinct films or layers, the elastic characteristics of the stored energy means can be precisely tailored. The multi-layered or gradient construction of laminate 35 also permits venting to atmosphere through the laminate surface certain selected, entrained gases or vapors contained within the reservoir while simultaneously precluding any negative migration of selected atmospheric gases or vapors into the reservoir.

In constructing laminate 35 for certain applications, layer 35a may comprise a thin film barrier structure of a first thickness which is substantially impermeable to oxygen, while layer 35b may comprise a thin elastomer film of a second thickness. Layer 35c may be of still a different construction and, for example, may comprise an interfacial biocompatible material which has predetermined elastic characteristics.

For other applications where the reservoir is intended to be free venting, the upper or layer 35a of laminate 35 may have a first selected permeability while layer 35b may have a second selected permeability. Layer 35c may be of still a different thickness and permeability and may have the perm-select characteristics best suited for the end application to be made of the device. The selective arrangement of the different films, or membranes which make up the laminate, each with its own individual characteristics, such as permeability and thickness, permits the design of a stored energy source that is precisely tailored for the particular use to be made of the mixing apparatus.

As indicated in FIG. 3, laminate 35 overlays base 16 and, as before, is enclosed within a cover assembly 37 of the character described in detail in Ser. No. 08/054,152 having a medicament label 37a. Materials suitable for the construction of this assembly will presently be described.

Figure 6:
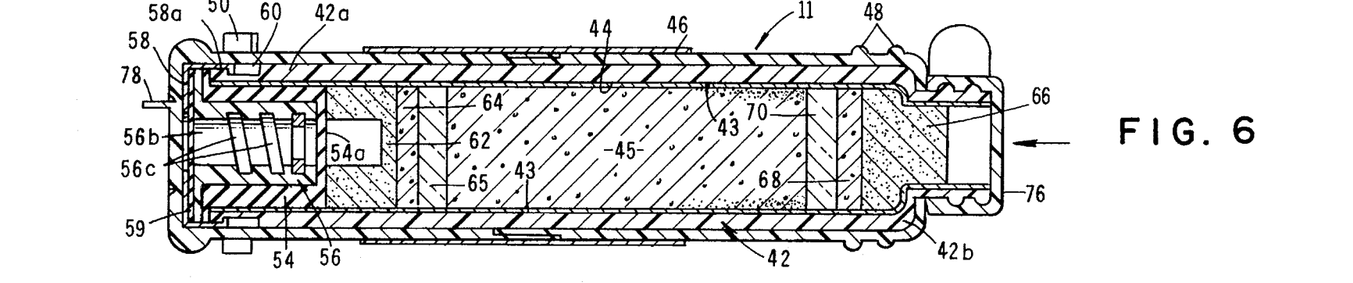
FIG. 6 is a side-elevational, cross-sectional view of one form of the vial assembly portion of the device of the invention.

Turning now particularly to FIGS. 5 and 6, the vial assembly 11 of the present form of the invention comprises a vial 42 having a chamber 44 for containing the additive 45. A two-part plastic cover, or overpackage 46, is closely received over vial 42 and is provided with external threads 48 and system interlock stops 50. Threads 48 are adapted to mate with internal threads 52 provided on cylindrical housing portion 12. The manner of interconnection of the vial assembly and the housing will presently be discussed.

Vial 42 of the vial assembly can be constructed of glass or plastic depending upon the application to be made of the apparatus. When the container is formed of a plastic material having the inner surface thereof may be provided with covering means here shown in the form of a surface modification coating 43. The covering means, which may also be in the nature of a thin film, lengthens product shelf life and functions as a vapor and gas transmission barrier, having, for example, improved resistance to oxygen permeability. Coating 43 is here shown as a functional coating comprising a thin film having vapor barrier properties. In the preferred form of the invention, a silicon oxide based film is deposited on the inner surface of the plastic vial. Various base plastics such as poly (ethyleneterephthalate (PET) base material, and can be subsequently treated by the plasma deposition of silicon oxide.

Alternate forms of coating 43 include functional composite coatings of aluminum oxide and silicon dioxide, or multilayer films of plasma deposited Hydrogenated Amophous silicon (a -s::H) and silicon nitride, and other layering of micro crystalline silicon (mu c-sl) deposition.

Figure 6A:
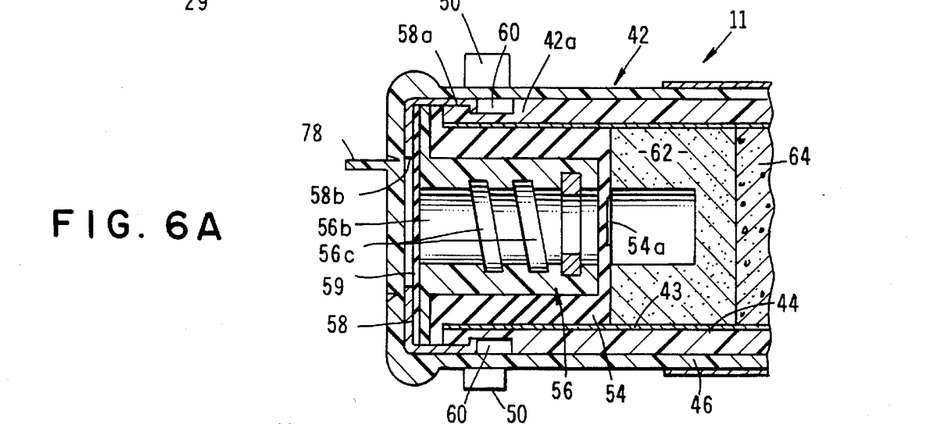
FIG. 6A is an enlarged, cross-sectional view of the outlet portion of the vial assembly showing more clearly the construction of the crimp cap assembly.

The outboard end 42a of vial 42 is closed by an elastomeric sealing member 54 which is provided with a centrally disposed, rupturable membrane 54a that, when ruptured, permits communication between chamber 44, which contains the additive and the exterior of the vial assembly. Sealing member 54 is secured in position within end 42a of the vial by a plastic housing 56 and an aluminum crimp cap 58 having a peripheral end portion 58a that can be crimped into a groove 60 formed in vial 42. As best seen in FIG. 6A, crimp cap 58 has a central aperture 58b which exposes a thin pierceable rubber or silicon disk 59 that can be bonded to the outer flange surface of member 56. Disposed snugly within vial 42 proximate member 54 is a porous distribution plug 62 which functions to distribute the fluid flowing from chamber 44 toward membrane 54a via a flow rate control element 64 and a glass frit 65 both of which are snugly disposed within the vial between plug 62 and the additive 45 in the manner best seen in FIG. 6. Element 64 can be any type of porous disk that functions to control the rate of fluid flow from the device. In a manner presently to be described, element 64 also functions to control the dwell time of the fluid within chamber 44.

The opposite end 42b of vial 42 is also closed by a porous plug 66 of a character similar to plug 62. Disposed between plug 66 and additive 45 is a second rate control member 68 and a second glass frit 70 which are snugly fit within vial 42. Member 68 cooperates with member 64 to control dwell time of the fluid within chamber 44 so as to insure complete mixing of the fluid component with the additive 45. It is to be appreciated that, members 64 and 68 cooperate to create a selected differential pressure within chamber 44 so that the delivery flow rate of the fluid mixture from the device can be precisely controlled. Additionally, by selecting appropriate adding means which exhibits the desired timed release disassociation of the additive from the additive presentation means, alternate drug dosing rates, i.e., alternate drug concentrations can be readily achieved. Rate control member 68, like member 64, can be any type of porous disc that will precisely control the rate of fluid flow toward chamber 44. The various materials suitable for use in the construction of the porous plugs, the glass frits, and the rate control members are discussed in Ser. No. 08/054,152 which is incorporated herein by reference.

The adding means of the embodiment of the invention shown in FIGS. 5 and 6 is provided in the form of a cylindrically shaped, porous functional support structure which is carried within chamber 44 and to which various additives including beneficial agents such as drugs, biologically active materials and chemical elements and compounds can be releasably connected in the manner described in Ser. No. 06/054,152. These additives are carried by the structure in a manner such that, as the liquid flows through chamber 44 and circulates around, about and through the support assembly, the additives will efficiently be removed from the support and mixed with the liquid flowing into the chamber from the previously charged reservoir R. It is to be understood that the adding means disposed within chamber 44 can be of the general character of any one, or a combination of, those illustrated in FIG. 66 of Ser. No. 08/054,152.

In operating the apparatus of this latest form of the invention, the reservoir R is charged with fluid F by introducing the fluid into the reservoir vial luer connector L and inlet port 28. In a free venting system, air within the reservoir will be vented through hydrophobic vent means, shown here as vent 29, provided in the cover. In nonventing stored energy membrane systems, air between the stored energy means and the cover will be vented through the vent means. The fluid under pressure flowing through port 28 will cause the stored energy means, or laminate 35, to move from its relaxed or semi-relaxed starting state (i.e., zero tension or pretensioned) to the operative configuration shown in FIG. 5, In this operative state, the stored energy means will have a tendency to return to its starting configuration and in so doing will cause fluid contained within the reservoir to flow outwardly through the fluid outlet passageway 22 and toward valve means V urging it into a closed position.

After the reservoir is charged, the sterile vial closure cap 76, which is provided proximate the threaded end of the vial assembly, as well as a sterile closure cap which closes the open end of cylindrical portion 12, are both removed and discarded. As the vial assembly is inserted into open end 12a of portion 12, threads 48 will move toward engagement with threads 52 provided within housing body 12. Rotation of the vial assembly in a clockwise direction will cause the vial to advance within cylindrical portion 12 to the position shown in FIG. 5. As the vial assembly seats within the coupling means, the valve means, here shown as valve member V-1, will move away from valve seats V-2 formed in wall 20. Additionally, as the vial assembly seats within portion 12, locking tabs 50 will lockably engage the locking fingers 77 provided on portion 12 so as to prevent removal of the vial assembly from the dispenser unit.

Figure 7:
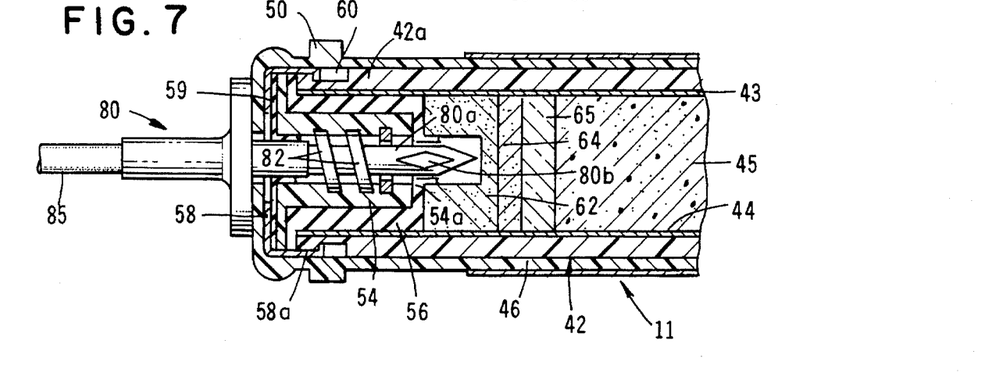
FIG. 7 is a fragmentary, side-elevational, cross-sectional view of the outlet end of the vial assembly showing a delivery spike penetrating an elastomeric closure plug mounted within the vial assembly.

With the drug vial assembly in place within cylindrical portion 12 and with the reservoir R charged with the liquid, closure cap 78 provided on the outboard end of the vial subassembly is removed (FIG. 2). This done, the delivery spike 80 is inserted through the aperture 58b in crimp cap 58, through pierceable disk 59, and into the central passageway 56b formed in member 56. As best seen in FIG. 7, shank 80a of the delivery spike is provided with threads 82 which are adapted to mate with internal threads 56c provided on member 56. As the delivery spike is threadably advanced within passageway 56b, the apertured point of the delivery spike will pierce membrane 54a permitting fluid to flow from chamber 44 into apertures 80b, through spike 80 and then into a connector 85 which is connected to the delivery spike.

Turning now to FIGS. 8 through 11, another embodiment of the invention is there shown. In this embodiment, the construction of the cylindrical housing portion 12 and the base assembly 10 are of similar construction to that shown in FIGS. 1 through 7 and like numbers are used to designate like components. However, the stored energy means, the details of construction of which will presently be described, is of completely different construction. More particularly, in the apparatus of this latest form of the invention, the distendable membrane laminate assembly does not act as the primary stored energy source, but rather serves as a barrier member which engages and is moved by an expandable member which has a number of unique characteristics that will presently be described.

Save for the fact that the energy source is different, the intermixing process as previously described in connection with FIGS. 1 through 7 remains substantially the same as does the adding means of the invention.

Figure 8:
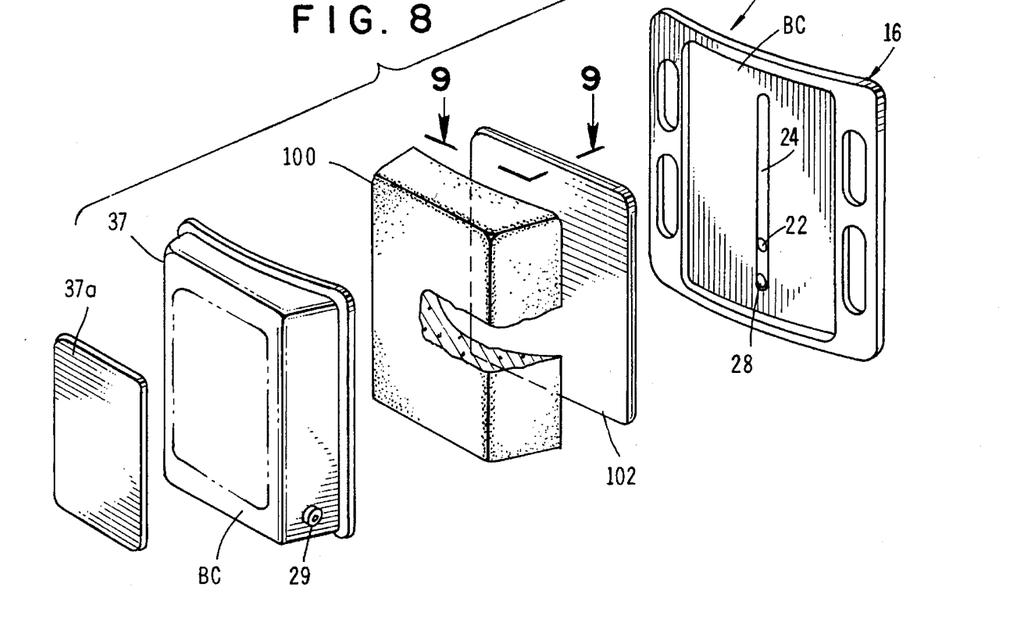
FIG. 8 is a generally perspective, exploded view of the dispensing portion of an alternate embodiment of the invention.
Figure 9:
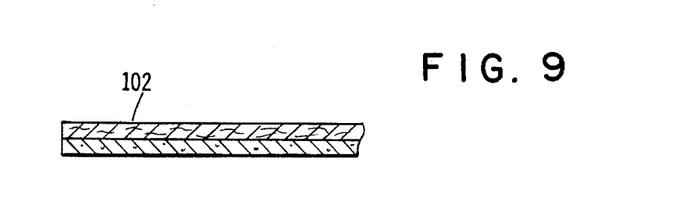
FIG. 9 is a greatly enlarged cross-sectional view taken along lines 9—9 of FIG. 8.
Figure 10:
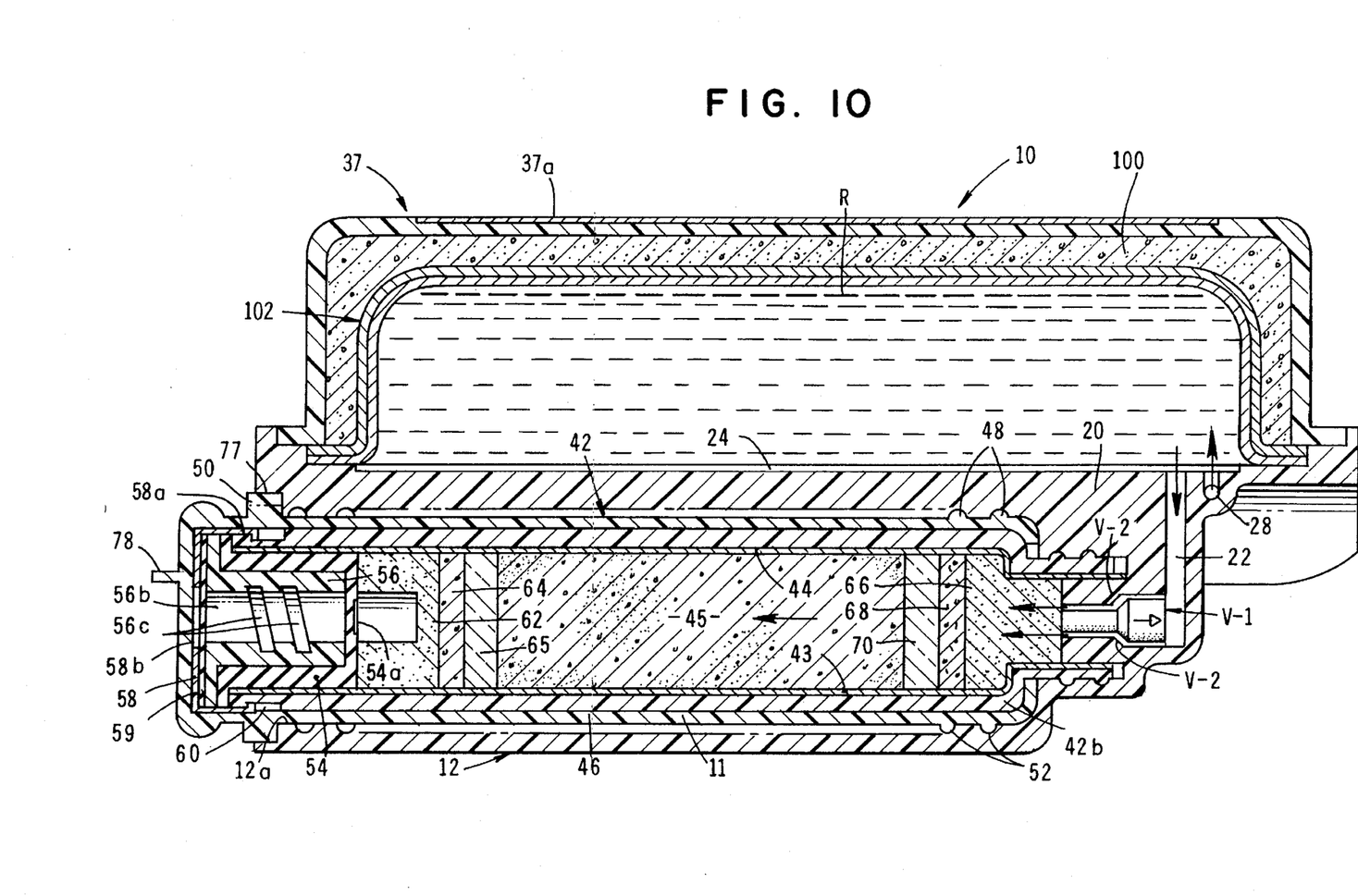
FIG. 10 is a greatly enlarged, side-elevational, cross-sectional view of the device of this latest embodiment of the invention shown with the vial assembly portion operably interconnected with the dispensing portion.

Turning particularly to FIGS. 8 and 10, the stored energy means of this latest form of the invention is shown as a flexible elastic cellular mass, such as a sponge like polymeric foam member 100 and the barrier means which is acted upon by the member to expel fluid from the reservoir R is identified as deformable laminate 102. Expandable member 100, which is preferably compressible, elastically deformable, and highly resilient, can be constructed from a wide variety of materials, including a number of flexible cellular polymers. Materials that are particularly attractive for this application include polyurethane, latex foam rubber, cellular rubber, foamed polymers, various polyolefin foams, PVC foams, epoxy foams, urea formaldehyde, silicon foam, fluropolymer foams, and other elastic syntactic foams, elastomers and similar materials of a character well understood by those skilled in the art. Member 100 can be monolithic or it can be constructed from homogeneous or nonhomogeneous foam or laminates having the same or different characteristics. In FIG. 10, member 100 is shown in a substantially compressed state and ready to expand against deformable barrier member 102 to urge the fluid contained within the reservoir R outwardly from the reservoir in a manner presently to be described.

Barrier laminate 102, which may be two or more membranes, a film, a skin, or a multilayer laminate can also be constructed from a wide variety of permeable and nonpermeable materials including those previously defined in connection with the description of laminate 35. It is to be understood that laminate 102 can be separate from or interconnected with the outer interface of the energy source 100. In some instances, laminate 102 can be integrally formed with member 100 as a skin-like attachment and may exhibit elastomeric characteristics.

In operating the apparatus of this latest form of the invention, reservoir is filled in the manner previously described through luer filling L and inlet 28. During this filing step, valve V-1 is sealed against valve seal V-2. As fluid enters the reservoir, it will impinge upon laminate or barrier 102 and barrier 102 will, in turn, compress compressible and expandable member 100 (FIG. 10). In its compressed operative state, member 100 becomes the energy source to later expel the fluid from the reservoir. As before, air within the reservoir will be vented through the hydrophobic vent means or vent 29.

After the reservoir has been charged, the sterile vial closure cap 76, as well as the sterile closure cap which closes the open end of cylindrical portion 12, are removed and discarded. As the vial assembly is inserted into open end 12a of portion 12, threads 48 will move toward engagement with threads 52 provided within housing body 12. Rotation of the vial assembly in a clockwise direction will cause the vial to advance within cylindrical portion 12 to the position shown in FIG. 10. As the vial assembly seats within the coupling means, the valve means, or valve member V-1, will move away from valve seats V-2 formed in wall 20 and locking tabs 50 will lockably engage the locking fingers 77 so as to prevent removal of the vial assembly from the dispenser unit.

Figure 11:
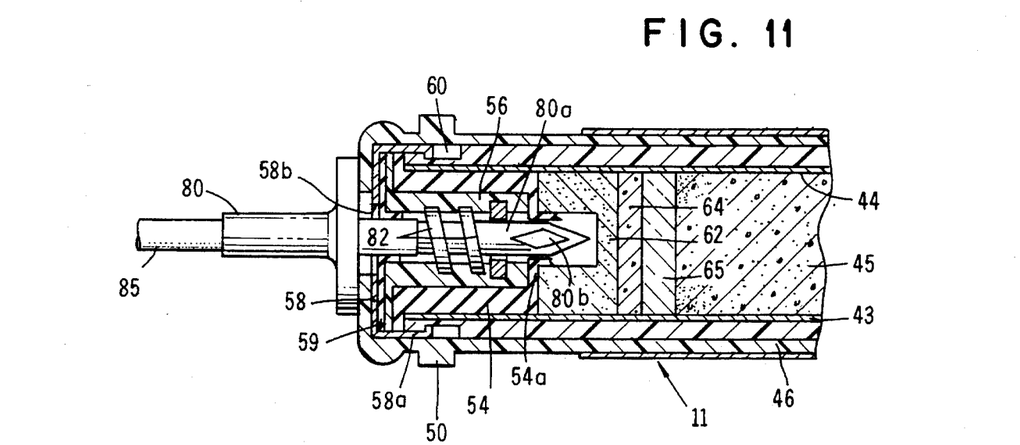
FIG. 11 is a fragmentary, side-elevational, cross-sectional view of the outlet end of the vial assembly of FIG. 10 showing a delivery spike penetrating an elastomeric closure plug mounted within vial assembly.

With the drug vial assembly in place within cylindrical portion 12 and with the reservoir R charged with the liquid, closure cap 78 provided on the outboard end of the vial subassembly is removed (FIG. 2). This done the delivery spike 80 is inserted through the central opening 58b in crimp cap 58, and through frangible disk 59 into the central passageway 56b formed in member 56. As the delivery spike is threadably advanced within passageway 56b, the apertured point of the delivery spike will pierce membrane 54a permitting fluid to flow from chamber 44 into apertures 80b, through spike 80 and then into a connector 85 which is connected to the delivery spike.

During the fluid delivery and mixing step, expandable member 100 will return toward its original starting configuration and in so doing will expel the fluid from the reservoir into outlet passageway 28, through the valve means and into chamber 44 for mixing with the additive. The mixture thus formed will then flow outwardly of the dispenser via delivery spike 80.

With either the embodiment shown in FIGS. 1 through 7 or the embodiment shown in FIGS. 8 through 11, the reservoir can be prefilled and stored in a filled condition until time of use. In this case, base member 16, the upper laminate of laminate 35 and in some cases the lower laminate of laminate 35, as well as cover 37 are preferably provided with thin barrier coatings BC, which are adapted to retard oxygen, carbondioxide, and moisture permeation. Coatings BC may also comprise thin films affixed to the members. Alternatively, base 16 and cover 37 can be constructed entirely from structural barrier materials which similarly have the ability to retard oxygen, carbondioxide and moisture permeation. Some of these materials can also provide an interfacial compatability surface which is compatible with the liquid components to which they are exposed. Materials suitable for the formation of the barrier coatings and the barrier materials comprise the previously identified vial coating materials as well as other unique polymers, including poly-para-xylylene and members of like polymer series which are offered by various companies, including Union Carbide under the name and style "Paralene".

Surface coatings of the character here contemplated can include single or multiple layers of similar or different materials. The interfacial coating, coatings, or films can be employed to increase the functional surface compatibility of the base material with the intended reservoir contents, the barrier properties of the base materials, including its gas permeation, migration and perm-select characteristics and for optimizing the morphology of the material for specific applications.

Materials suitable for the construction of base member and the cover include polycarbonate, high and low density polyethylene, polypropylene, nylon, polystyrene, polyamides, styrenes, PET, and various like materials.

The exterior surfaces of the cover assembly can also be provided with a negative permeation barrier means for preventing external migration of a penetrant into the interior of the cover. The materials used to form the barrier materials and coatings can also selectively comprise both rubber and glassy advance polymers, including thermoplastic films such as polyvinylchloride (PVC), copolymers of vinylidene chloride and vinylchloride, polyethylene terephthalate (PET), tetrafluoroethylenehexafluoropropylene and vinylidene flouride (THV fluoroplastic) ethylene, vinyl alcohol copolymers, advance amorphous polymers, including polyvinyl chloride and polystyrene. The coating can also be formed in a manner well understood by those skilled in the art, of plasma deposited silicon oxide, silicon dioxide, silicon nitride, aluminum oxide and silicon dioxide and various like materials.

Alternate materials suitable for constructing base 16 and cover 37 is a material sold by B-P chemicals International of Cleveland, Ohio, under the name and style "Barex". This material is a clear rubber-modified, Acrylonitrile Copolymer which has wide application in the packaging industry because of its superior gas barrier, chemical resistance and extrusion (thermoforming) and injection molding capabilities. Structures using this material can be manufactured in either monolayer or coextrusion (with such other materials as polyethylene, polypropylene, polystyrene and other modified styrenes). Combinations of different material can be used to enhance the desired physical properties of the thermoformed part.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A mixing apparatus comprising:
   (a) a container assembly including:
      (i) a container having a fluid inlet passageway, a fluid outlet passageway and walls defining an internal chamber in communication with said fluid inlet and outlet;
      (ii) adding means disposed within said chamber for adding an additive to fluid flowing through said chamber, said adding means comprising an additive and an additive presentation means for presenting said additive to the fluid;
   (b) a dispensing device comprising a housing having a fluid inlet port and first and second portions, said housing including a covering adapted to retard oxygen, carbon dioxide and moisture permeation, said first portion including coupling means for coupling said container assembly with said first portion of said housing, said coupling means having a flow passageway adapted to communicate with said fluid inlet passageway of said container;

said second portion comprising:
      (i) a base adapted to retard oxygen, carbon dioxide and moisture penetration, said base having a fluid outlet in communication with said flow passageway of said coupling means; and
      (ii) a stored energy means cooperating with said base to define a reservoir containing a fluid, said reservoir being in communication with said fluid inlet port and said fluid outlet of said base, said stored energy means being acted upon by fluid introduced into said reservoir under pressure to move it from a starting configuration to an operative configuration wherein it will have a tendency to return toward its starting configuration causing fluid contained within said reservoir to flow out said fluid outlet of said base and into said flow passageway of said coupling means in a direction toward said adding means.

2. A device as defined in claim 1 in which said covering of said housing and said base are coated with a barrier coating adapted to retard oxygen, carbon dioxide and moisture permeation.

3. A device as defined in claim 1 in which said stored energy means comprises a distendable membrane constructed of an elastic material and having a coating adapted to retard oxygen, carbon dioxide and moisture.

4. A device as defined in claim 1 in which said stored energy means comprises a deformable barrier member and an elastically deformable expandable member.

5. A device as defined in claim 1 in which said stored energy means comprises a distendable membrane constructed of an elastic material and a film connected thereto, said film being adapted to retard oxygen, carbon dioxide, and moisture permeation.

6. A mixing apparatus comprising:
   (a) a container assembly including:
      (i) a container having a fluid inlet passageway, a fluid outlet passageway and walls defining an internal chamber in communication with said fluid inlet and outlet;
      (ii) adding means disposed within said chamber for adding an additive to fluid flowing through said chamber, said adding means comprising an additive and an additive presentation means for presenting said additive to the fluid;
   (b) a dispensing device comprising a housing having a fluid inlet port and first and second portions, said first portion including coupling means coupling said container assembly with said first portion of said housing, said coupling means having a flow passageway adapted to communicate with said fluid inlet passageway of said container;

said second portion comprising:
      (i) a base having a fluid outlet in communication with said flow passageway of said coupling means; and
      (ii) a stored energy means cooperating with said base to define a reservoir for containing a fluid, said reservoir being in communication with said fluid inlet port and said fluid outlet of said base, said stored energy means being acted upon by fluid introduced into said reservoir under pressure to move it from a starting configuration to an operative configuration wherein it will have a tendency to return toward its starting configuration causing fluid contained within said reservoir to flow out said fluid outlet of said base and into said flow passageway of said coupling means in a direction toward said adding means.

7. A device as defined in claim 6 further including flow control means carried by said coupling means for controlling the flow of fluid through said flow passageway.

8. A device as defined in claim 6 in which said fluid inlet port of said dispensing device comprises a luer connector.

9. A device as defined in claim 6 in which said stored energy means comprises a distendable membrane constructed of an elastic material.

10. A device as defined in claim 6 in which said stored energy means comprises a deformable barrier member and an elastically deformable expandable member.

11. A device as defined in claim 6 further including accessing means operably associated with said container assembly for permitting fluid flow through said outlet passageway of said container.

12. A device as defined in claim 11 in which said accessing means comprises:

(a) a rupturable membrane sealably disposed within said container; and (b) means for rupturing said rupturable membrane.

13. A device as defined in claim 12 which said means for rupturing said rupturable membrane comprises a delivery spike.

14. A fluid mixing and infusion device (a) a container assembly including:
 (i) a container having a fluid inlet passageway, a fluid outlet passageway and walls defining an internal chamber in communication with said fluid inlet and outlet;
 (ii) adding means disposed within said chamber for adding an additive to fluid flowing through said chamber, said adding means comprising an additive and an additive presentation means for presenting said additive to the fluid;

(b) a dispensing device comprising a housing having a fluid inlet port and first and second portions, said first portion including coupling means coupling said container assembly with said first portion of said housing, said coupling means having a flow passageway adapted to communicate with said fluid inlet passageway of said container;

said second portion comprising:
 (i) a base having a fluid outlet in communication with said flow passageway of said coupling means; and
 (ii) a thin, generally planar distendable membrane constructed of an elastic material, said membrane being adapted to overlay said base and cooperate therewith to define a reservoir for containing a fluid, said reservoir being in communication with said fluid inlet port and said fluid outlet of said base, said membrane being distendable by fluid introduced into said reservoir under pressure and having a tendency to return to a substantially less distended configuration, whereby the fluid contained within said reservoir will be urged to flow out said fluid outlet of said base and into said flow passageway of said coupling means in a direction toward said adding means.

15. A device as defined in claim 14 in which said additive comprise a beneficial agent which is removable from said additive presentation means using affinity attachment chromatography techniques.

16. A device as defined in claim 14 in which said additive comprises a beneficial agent which is removable from said additive presentation means using bioseparation techniques.

17. A device as defined in claim 14 in which said additive is removably connected to said additive presentation means using azlactone functional compounds.

18. A device as defined in claim 14 in which said additive presentation means comprises a structural support disposed within said container, said structural support having biologically active proteins bound thereto.

19. A device as defined in claim 14 in which said container assembly further includes at least one flow rate control means for controlling the residence time of the fluid within said internal chamber of said container.

20. A device as defined in claim 14 in which said container includes at least one porous plug for controlling the path of flow of the fluid through said container.

21. A device as defined in claim 14 in which said base further includes vent means for venting air to atmosphere during filling of said reservoir and during dispensing of fluid from said device.

22. A device as defined in claim 14 further including flow control means carried by said coupling means for controlling the flow of fluid through said flow passageway.

23. A device as defined in claim 22 in which said coupling means includes a wall within which said flow passageway is formed and in which said flow control means comprises valve means for controlling fluid flow through said flow passageway and into said fluid inlet passageway of said container, said valve means comprising:

(a) a valve housing provided in said wall;

(b) a valve seat formed in said valve housing; and (c) a valve member movable from a first position in sealing engagement with said valve seat to a second position spaced apart from said valve seat.

24. A mixing apparatus comprising:

(a) a container assembly including:
 (i) a container having a fluid inlet passageway, a fluid outlet passageway and walls defining an internal chamber in communication with said fluid inlet and outlet;
 (ii) adding means disposed within said chamber for adding an additive to fluid flowing through said chamber, said adding means comprising an additive and an additive presentation means for presenting said additive to the fluid;

(b) a dispensing device comprising a housing having a fluid inlet port and first and second portions, said first portion including coupling means coupling said container assembly with said first portion of said housing, said coupling means having a flow passageway adapted to communicate with said fluid inlet passageway of said container;

said second portion comprising:
 (i) a base having a fluid outlet in communication with said flow passageway of said coupling means; and
 (ii) a deformable barrier member said member being adapted to overlay said base and cooperate therewith to define a reservoir for containing a fluid, said reservoir being in communication with said fluid inlet port and said fluid outlet port of said base, said barrier member being movable from first position to a second position in response to fluid being introduced into said reservoir through said fluid inlet port;

(c) an expandable member disposed in contact with said deformable barrier member, said expandable member being movable by said barrier member from a starting configuration to a second operative configuration wherein it will have a tendency to return toward its starting configuration causing fluid contained within said reservoir to flow out said fluid outlet of said base and into said flow passageway of said coupling means in a direction toward said adding means.

25. A device as defined in claim 24 in which said container includes flow rate control means for controlling dwell time of fluid within said chamber.

26. A device as defined in claim 24 in which said container includes flow rate control means for controlling the rate of flow of fluid through said fluid outlet passageway of said container.

27. A device as defined in claim 24 in which said adding means provides means for controlling additive dosing rates to fluid flowing through said chamber.

28. A device as defined in claim 24 further including flow control means carried by said coupling means for controlling the flow of fluid through said flow passageway.

29. A device as defined in claim 28 in which said fluid outlet passageway of said container is closed by a rupturable membrane.

\* \* \* \* \*